United States Patent [19]

Merrifield et al.

[11] Patent Number: 5,585,353

[45] Date of Patent: Dec. 17, 1996

[54] ANTIBIOTIC PEPTIDES CONTAINING D-AMINO ACIDS

[75] Inventors: Robert B. Merrifield, Creskill, N.J.; David Wade, New York, N.Y.; Hans G. Boman, Stockholm, Sweden

[73] Assignee: The Rockefeller University, New York, N.Y.

[21] Appl. No.: 307,479

[22] Filed: Sep. 16, 1994

Related U.S. Application Data

[63] Continuation of Ser. No. 87,143, Jul. 6, 1993, abandoned, which is a continuation of Ser. No. 474,524, Feb. 2, 1990, abandoned.

[51] Int. Cl.⁶ .......................... A61K 37/02; C07K 14/00
[52] U.S. Cl. .................................. 514/12; 530/324
[58] Field of Search ........................ 530/324; 514/12

[56] References Cited

U.S. PATENT DOCUMENTS

| | | | |
|---|---|---|---|
| 4,810,777 | 3/1989 | Zasloff | 530/326 |
| 4,962,277 | 10/1990 | Cueruo et al. | 530/324 |
| 5,114,921 | 5/1992 | Zasloff | 514/12 |
| 5,221,664 | 6/1993 | Berkowitz | 514/6 |
| 5,424,290 | 6/1995 | Maloy et al. | 514/13 |

OTHER PUBLICATIONS

Merrifield, et al, vol. 231, No. 2, Feb., 1988.
Fink, et al, J. Biol. Chem, vol. 264, No. 11 pp. 6260–6267, 1989.
Boman, et al, vol. 259, No. 1 pp. 103–106, 1989.
Hultmark, et al, European Journal of Biochemistry, vol. 127, pp. 207–217 (1982).
Zasloff, Proc. Natl. Acad. Sci. USA, vol. 84, pp. 5449–5453, 1987.

Primary Examiner—Elizabeth C. Weimar
Assistant Examiner—S. G. Marshall
Attorney, Agent, or Firm—Klauber & Jackson

[57] ABSTRACT

Antibiotically and/or antimalarially active D-peptides of naturally occurring antibiotics such as cecropin A, B and D, melittin, and Magainin I and II and their addition, deletion and replacement analogs including homologous and heterologous analogs thereof.

7 Claims, 1 Drawing Sheet

5,585,353

1

ANTIBIOTIC PEPTIDES CONTAINING D-AMINO ACIDS

This invention was made with Government support under DK 01260 awarded by the National Institutes of Health. The Government has certain rights in the invention.

This application is continuation of application Ser. No.: 08/087,143 filed: Jul. 6, 1993, now abandoned, which is a continuation application of application Ser. No. 07/474,524, filed Feb. 2, 1990 now abandoned.

This application contains subject matter which is related to patent application Ser. No. 07/449,593 filed Dec. 12, 1990. The complete disclosure of this application is hereby incorporated herein.

BACKGROUND OF THE INVENTION

Several naturally occurring, antibiotically active peptides with useful therapeutic activity against pathogenic bacteria and other classes of microorganisms have recently been identified and isolated from insects, frogs and higher animals. These include cecropins, attacins, magainins, sarcotoxin, sapecin, bactenecins, alamethicins, defensins and PGLa.

Other naturally occuring peptides from microorganisms, from insects and from higher animals are generally known as toxins because they lyse red blood cells as well as other eukaryotic cells. These toxins include different hemolysins such as streptolysins, melittin, barbatolysin, paradaxins and delta hemolysin. It is known but it is not widely recognized that some toxins like melittin will also kill bacteria. Therefore, for purposes of this description they will be described as antibiotically active peptides.

The invention described and claimed in the above identified related application is based on the unexpected discovery that novel antibiotic molecules can be constructed by joining together at least two amino acid sequences from different antibiotic peptides. One advantage of such hybrid molecules is that they may be constructed to be shorter and therefore easier to synthesize than the natural peptides from which they are derived.

The hybrid peptides, in addition to their antibiotic activity, appear to have other features in common. For example they all contain about 20 to 40 amino acids and often they are more effective if their C-terminals are amidated or blocked in other ways. They are therefore potential candidates for commercial preparation by solid phase synthesis. Additionally, they all appear to contain certain sequences of amino acids which impart specific conformations, i.e. secondary structural characteristics to portions of the molecule. Often the N-terminal region is hydrophilic and basic, and the C-terminal region is hydrophobic. Some portions of the molecule have a tendency towards helicity, others do not. Some molecules contain relatively long sequences which are flexible, thus forming hinge regions in the molecule. Often the helical portions are amphipathic, i.e., they are characterized by a hydrophilic and a hydrophobic surface.

These antibiotics appear to function by forming ion channels in the cell membrane of the bacteria, or other organism which then leads to rupture of the membrane and then rupturing of the cell. They have been characterized as lytic or channel forming antibiotics. Binding of the peptides to the membrane results in the formation of channels which permit entry of ions through the channels into the cellular fluid. This increases the osmotic pressure of the cell and causes more fluid to enter it. The increase in internal pressure causes the cell to burst. The differing secondary characteristics of the various portions of the antibiotic peptides appear to be associated with their mode of action in penetrating the cell membrane and lysing the cell.

A very important current medical problem is to find antibiotics with enhanced potency against human pathogens, especially those for which no suitable antibiotic is now available or to which resistant organisms have emerged. One response to the emergence of organisms resistant to antibiotics has been to prepare synthetic derivatives of the antibiotics, but this approach has been limited by the availability of functional groups on the parent molecule that can be utilized as foci for preparing derivatives.

It would be useful to have available a pool of antibiotics of comparatively simple structure which could be synthesized with relative ease, and which at the same time would be susceptible to structural variations for the purpose of producing analogs useful against specific organisms for which no non-toxic antibiotic is presently available, or for improving activity against other organisms for which the presently available antibiotics are toxic to the host. Such compounds should also have sufficient in vivo stability to resist degradation by mammalian enzymes.

It has been discovered, as described in the above identified patent application, that naturally occurring peptides such as those mentioned above, and others like them, constitute such a pool. In these compounds all of the amino acid residues are in the L-, or natural form.

THE INVENTION

Figure 1:
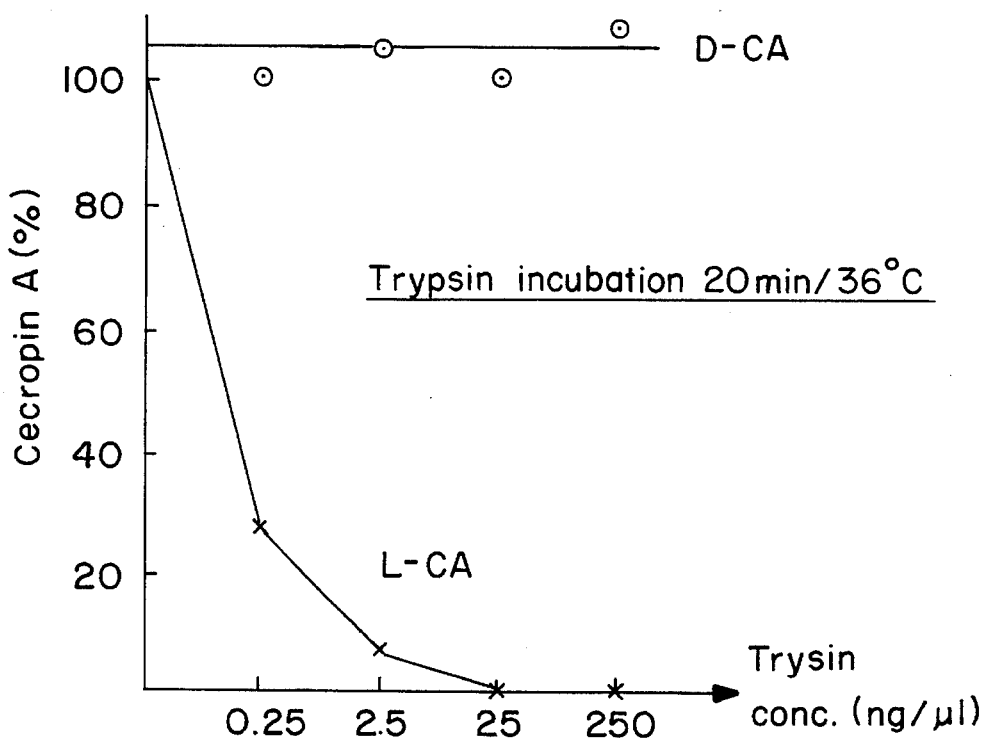
FIG. 1 is a graph comparing the stability of cecropin A in which all of the amino acid residues are in the L-form with its enantiomer in which all of the amino acid residues are in the D-form when the products are separately incubated with trypsin.

Novel, synthetic antibiotically and/or antimalarially active, non-toxic peptides that are D enantiomers of active antibacterial peptides related in amino acid sequence to the naturally occurring peptides containing from about 20 to about 40 amino acid residues have now been discovered. These channel forming antibiotics are similar in primary structure to the corresponding natural antibiotics or to the hybrid products of the prior application or to other analogs of the natural antibodies except that the amino acid residues of the products of this invention are all, or substantially all, in the D-configuration. They have been shown to possess equal but opposite conformations relative to all L-peptides, i.e. They are enantiomers or mirror images.

As with the products of the previous invention, the structures contain a hydrophilic or basic segment, often the N-terminal segment and a hydrophobic segment, often at the C-terminus. Some portions of the molecule have helical potential, others do not. Some of the antibiotic peptides of this invention contain relatively long sequences which are flexible and form hinge regions. The helical portions may be amphipathic. The products of this invention are, in fact, mirror images, or substantially mirror images of the products of the prior invention. The products of the invention also include mirror images, or substantial mirror images, of the naturally occurring antibiotic peptides such as cecropin, magainin or and melittin. Thus, the products of this invention are enantiomers or substantially enantiomers of the products of the previous invention. All or substantially all of the amino acid residues in the products of this invention are in the D-form. A limited number, usually not more than about 5 to 8, may be in the L-form provided that the resulting products substantially retain their mirror imagery with products in which all of the amino acid residues are in the L-form. It will be apparent to those skilled in the art that the degree to which mirror imagery is lost will depend upon the amino acids present in the molecule and their sequence. Some products of the invention may include a relatively large number of L-amino acids, while others lose their activity when even one of the amino acid residues is in the L-form.

Both the L- and the D- forms of these peptides are lytic and produce electrically conducting channels or pores in lipid bilayers and this is believed to be the mechanism by which they promote their antibacterial activity.

The products of this invention are especially useful because they retain the therapeutic activity of their enantiomers, but unlike the L-form products, they do not have the disadvantage of being susceptible to enzymatic hydrolysis by naturally occurring mammalian enzymes. Therefore, therapeutic levels of the antibiotic may be retained in the body for extended period of times, much longer than in the case of the L-form products. The resistance to enzymatic hydrolysis of the products of the invention is particularly advantageous because it permits them to be administered orally. They are not destroyed by the enzymes of the gastrointestinal system and, because they are relatively small, are absorbed before they are destroyed by the strong acidity of the gastric environment. Additionally, they are not antigenic.

The therapeutically useful peptides of this invention are characterized as the D-forms of naturally occurring antibiotically active peptides such as cecropin, magainin or melittin, or as D-forms of analogs and hybrids of these naturally occurring peptide including their replacement, addition and deletion analogs. The analogs may differ from the natural peptides by several amino acid residues.

When reference is made herein to the D-form of an antibiotic peptide it should be understood to mean that all or substantially all of the amino acid residues are in the D-form so that the product is a mirror image, or substantially a mirror image of the corresponding product in which all amino acid residues are in the L-form and that the two structures are not superimposable. Those skilled in the art will appreciate that it is most surprising to find that the therapeutic activity of an L-form of a linear channel forming antibiotice is retained in the corresponding D-form antibiotics.

This invention will be better understood by consideration of the application of the structure of cecropins, magainins and melittin.

The cecropins are a family of basic antibacterial peptides produced by the humoral immune response of certain insects as described in U.S. Pat. No. 4,355,104. They are also produced by mammals and are widely distributed in nature. Cecropins, together with attacins and lysozyme, are induced in the hemolymph of the pupae of the giant silk moth *Hylophora cecropia* following injection of live bacteria. There are three major cecropins, A, B and D. There is a high degree of sequence homology between them, and all are of about the same size (cecropin A: 37 residues, cecropin B: 35 residues, cecropin D: 36 residues). They each contain a hydrophilic amino terminal segment and a hydrophobic amidated carboxyl terminus.

The amino acid sequences of cecropin A, B and D are shown in Table 1 which also includes the sequences of magainin and melittin. For convenience and ease of analysis the cecropin molecules have been divided into three sections: residues 1–11, 12–24 and 25 to the end. Those skilled in the art will recognize the high degree of homology and that cecropins A and B will be quite similar in their secondary structures. Both would be expected to have a strong potential in a nonpolar environment to form an N-terminal amphipathic α-helix. The C-terminal segment will also have a tendency towards α-helix formation. In the central segment 12–24, there is some tendency for β-turns, for instance at residues 12–15, 15–18, 21–24. The N-terminal segment of cecropin D is less basic than either A or B. However, the central region of cecropin D has a higher potential for an α-helix than the central region of the A and B forms and also a stronger preference for a helix formation in the C-terminal region.

In summary, the cecropins have a strongly hydrophilic, amphipathic, α-helix at the N-terminus, a more hydrophobic α-helix at the C-terminus, and a flexible, structurally less defined central region with some potential for β-turns.

The structure of melittin, an antibacterial peptide isolated from bee venom is shown in Table 1. It is a basic amphipathic peptide in which residues 1–20 are predominantly hydrophobic and residues 21 to 26 are hydrophilic and basic. It will be noted that the arrangement of hydrophilic and hydrophobic regions are arranged opposite from the cecropins. In melittin, they are hydrophobic/hydrophilic, and in the cecropins they are hydrophilic/hydrophobic. In the middle of the molecule there is a Gly-Leu-Pro region which may act as a hinge. Melittin has potent antibiotic activity, but is not useful for mammals because it is lytic for leukocytes, erythrocytes and a wide variety of other cells.

Magainins 1 and 2 are 23-residue peptides isolated from frog skin. They each contain 3 or 4 lysine residues and each has a net positive charge. Both peptides have carboxyl, not amide, functional groups at amino acid number 23 terminus. There are only 2 differences between Mag 1 and Mag 2. These are at positions 10 and 22. Source of structure information is M. Zasloff, Proceedings of the National Academy of Sciences USA, August 1987, Vol.84, pages 5449–5453.

TABLE 1

Cecropin A:

H—Lys—Trp—Lys—Leu—Phe—Lys—Lys—Ile—Glu—Lys—Val—Gly—Gln—Asn—
Ile—Arg—Asp—Gly—Ile—Ile—Lys—Ala—Gly—Pro—Ala—Val—Ala—Val—Val—Gly—
Gln—Ala—Thr—Gln—Ile—Ala—Lys—NH$_2$

Cecropin B:

H—Lys—Trp—Lys—Val—Phe—Lys—Lys—Ile—Glu—Lys—Met—Gly—Arg—Asn—
Ile—Arg—Asn—Gly—Ile—Val—Lys—Ala—Gly—Pro—Ala—Ile—Ala—Val—Leu—Gly—

TABLE 1-continued

Glu—Ala—Lys—Ala—Leu—NH₂
Cecropin D:

H—Trp—Asn—Pro—Phe—Lys—Glu—Leu—Glu—Lys—Val—Gly—Gln—Arg—Val—
Arg—Asp—Ala—Val—Ile—Ser—Ala—Gly—Pro—Ala—Val—Ala—Thr—Val—Ala—Gln—
Ala—Thr—Ala—Leu—Ala—Lys—NH₂
Melittin:

H—Gly—Ile—Gly—Ala—Val—Leu—Lys—Val—Leu—Thr—Thr—Gly—Leu—Pro—
Ala—Leu—Ile—Ser—Trp—Ile—Lys—Arg—Lys—Arg—Gln—Gln(NH₂)
Magainin 1:

H—Gly—Ile—Gly—Lys—Phe—Leu—His—Ser—Ala—<u>Gly</u>—Lys—Phe—Gly—Lys—
Ala—Phe—Val—Gly—Glu—Ile—Met—<u>Lys</u>—Ser—OH
Magainin 2:

H—Gly—Ile—Gly—Lys—Phe—Lue—His—Ser—Ala—<u>Lys</u>—Lys—Phe—Gly—Lys—
Ala—Phe—Val—Gly—Glu—Ile—Met—<u>Asn</u>—Ser—OH

Peptides which are substitution, deletion or addition analogs of the foregoing peptides in which about 1 to about 12 of the amino acid residues differ from those in the naturally occurring peptides are particularly favored in the practice of this invention.

What has been said concerning the primary and secondary structural characteristics of melittin, magainin and the cecropins is equally applicable to the D-form of these channel forming antibiotics, and these D-form compounds and the various analog forms are within the ambit of this invention. These analogs include hybrids in which the positions of hydrophilic and hydrophobic segments of the antibiotic are reversed (homologous analogs) and others in which the hydrophobic segment is from one antibiotic and the hydrophilic from another (heterologous analogs).

It should be understood that in the following discussion, when reference is made to amino acids, amino acid residues, antibiotics or antibiotically active peptides, it is the D-form that is under discussion.

As indicated above, this invention includes not only addition, replacement and deletion analogs, but also hybrid analogs of naturally occurring antibiotics within its scope. Such antibiotically active hybrid peptides are prepared by rearranging selected regions or sequences of peptides such as those from melittin or a cecropin (D-forms), or in some instances adding a new region to the intact region of melittin, cecropin or the like. Thus a peptide formed by uniting the first 13 amino acid residues of D-cecropin A as the amino terminus with the first 13 amino acid residues of D-melittin; D-[CA(1–13)M(1–13)] is a useful product of this invention.

Often the analogs have improved pharmaceutical activity compared to the compounds which correspond exactly in amino acid sequence to the naturally occurring products.

The term "improving the pharmaceutical activity" as used herein means that the novel peptide is less toxic to mammalian cells and/or more active against a broader spectrum of pathogens or against a specific pathogen than a naturally occurring peptide from which it is derived. A peptide of the invention is said to be "derived" from a naturally occurring peptide if it contains at least one segment of amino acid sequences which is identical or substantially homologous to a region on a naturally occurring (L-form) peptide. Thus D-[CA(1–13) M(1–13)] can be considered as derived from both cecropin A and melittin. Other peptides within the scope of the invention may contain, for example, sequences from a magainin and an attacin, rearranged regions of a single antibiotic, for example melittin, or one region from a cecropin and another wholly unnatural region or may contain only one or a few changes relative to the all D forms of the natural sequence.

It will be apparent to those skilled in the art that the selected region of the "naturally occurring" peptide (D-form) in the final novel products of the invention does not need to be identical in amino acid sequence with the region in the natural peptide. One or more of the amino acid residues of the natural peptide may be replaced with another amino acid selected to increase the basicity, to interrupt the helicity or for any other useful reason. The sequence of amino acid residues in the novel product will, however, be substantially similar to the natural sequence.

The peptides of the invention will normally contain from about 20 to about 40 amino acid residues but are not so limited. One reason is that antibiotically active low molecular weight peptides usually contain a minimum of about 20 amino acids. Another, is that peptides with more than about 40 amino acids are relatively difficult to synthesize in pure form by chemical synthesis. A particular advantage of the useful peptides of this invention is that they are readily synthesized by solid phase methods and a variety of combinations are possible to achieve specifically required results. An advantage of the use of solid phase techniques is that the product can be readily synthesized with the C-terminus amidated or otherwise blocked.

The term "region" as used herein is similar to "segment" or "fragment". It refers to amino acid sequences normally containing from about 5 to about 20 amino acids. A "region" is usually selected or constructed to be flexible, basic, acidic, hydrophobic, hydrophilic or amphipathic these may form structures that consist of helices, G-sheets, turns or random coils. These properties and conformations will characterize the region. A hybrid molecule may be constructed to have at least two regions and may or may not contain a hinge region. The region does not need to be derived from a naturally occurring antibiotically active peptide containing 20 to 40 amino acid residues. It may be derived from a peptide containing less than 20 or more than 40 such residues.

The invention, then, comprises antibiotically and/or antimalarially active D-form peptides having antibiotic and/or antimalarial activity associated with channel formation normally containing from about 20 to about 40 amino acid residues including at least one region that is substantially similar to a corresponding sequence on a naturally occurring antibiotically and/or antimalarially active peptide of which the novel peptide is a mirror image or substantially a mirror image, and may be combined with one or more other peptide regions which may be from the same or another natural antibiotic and/or antimalarial peptide to form a hybrid molecule.

Typical compounds within the scope of this invention may be represented by the following list wherein C represents cecropin, CA, CB and CD represent the A, B and D forms of cecropin, M represents melittin and Mag represents magainin. The numbers represent the sequence of amino acid residues in the corresponding region of the natural peptide. "D" indicates the stereo configuration of the amino acids. The notations define the characteristics of the region.

| | |
|---|---|
| D-[CA(1–13)Mag(13–23)]- | hydrophilic/hydrophobic |
| D-[Mag$_2$(13–23)CA(1–13)]- | hydrophobic/hydrophilic |
| D-[Mag$_2$(13–23)M(15–26)]- | hydrophobic/hydrophobic |
| D-[M(1–13)CB(1–13)]- | hydrophobic/hydrophilic |
| D-[M(1–12)ProCA(1–13)]- | hydrophobic-Pro-hydrophilic |
| D-[M(1–15)C(1–11)]- | hydrophobic/hydrophilic |
| D-[M(16–26)CA(14–37)]- | hydrophobic/hydrophilic |
| D-[CA(25–36)ProCA(1–13)]- | hydrophobic-Pro-hydrophilic |
| D-[CA(25–37)CA(1–13)]- | hydrophobic/hydrophilic |
| D-[CA(1–24)M(1–13)]- | hydrophilic/hydrophobic |
| D-[CA(1–13)M(1–13)]- | hydrophilic/hydrophobic |
| D-[M(16–26)M(1–13)]- | hydrophobic/hydrophobic |
| D-[M(16–26)CA(23–37)]- | hydrophilic/hydrophobic |
| D-[CA(1–24)M(16–26)]- | hydrophilic/hydrophilic |
| D-[CB(25–35)M(14–26)]- | hydrophobic/hydrophilic |
| D-[CA(1–11)CD(12–37)]- | hydrophilic/hydrophobic |
| D-[CA(1–8)M(1–18)]- | hydrophilic/hydrophobic |
| D-[CA(1–9)M(1–17)]- | hydrophilic/hydrophobic |
| D-[CB(1–13)M(1–13)]- | hydrophilic/hydrophobic |
| D-[CA(1–17)M(1–9)]- | hydrophilic/hydrophobic |
| D-[CA(1–18)M(1–8)]- | hydrophilic/hydrophobic |
| D-[M(1–13)CA(1–22)]- | hydrophobic/hydrophilic |
| D-[M(1–13)CA(1–13)]- | hydrophobic/hydrophilic |
| D-[CA(1–13)M(1–13)]- | hydrophilic/hydrophobic |
| D-[CA(1–13)Mag$_2$(13–23)]- | hydrophilic/hydrophobic |
| D-[M(15–26)Mag$_2$(13–23)]- | hydrophobic/hydrophobic |
| D-[M(16–26)M(1–13)]- | hydrophobic/hydrophobic |
| D-[Mag$_2$(13–23)Mag$_2$(1–12)]- | hydrophobic/hydrophilic |

Other analogs within the scope of the invention include:

D-[Phe$^2$]CA in which the tryptophan at the 2-position of CA is replaced with phenylalanine, D-[Pro$^8$]CA in which the insoleucine at the 8-position of CA is replaced with proline, D-CA-OH in which the amide group of CA is hydrolyzed to carboxyl.

D-[Glu$^7$]M in which the lysine at the 7-position of melittin is replaced with glutamic acid, and D-[des Glu$^{19}$]Mag2 in which the glutamic acid at the 19-position of magainin 2 is deleted.

Most of the above products, in addition to being hydrophobic/hydrophilic or vice-versa will also have regions of helicity or amphipathicity. Proline (Pro) is often employed to interrupt a helix, although other amino acids may be similarly employed. The above peptides can also be constructed to include a flexible or hinge turn or bend region or regions of flexibility.

The compounds of this invention are synthesized by standard solid phase procedures with D-amino acids using the protection, deprotection and cleavage techniques and reagents appropriate to each specific amino acid or peptide. A combination of manual and automated (e.g., Applied Biosystem 430A) solid phase techniques can be used to synthesize the novel peptides of this invention although less convenient, classical methods of peptide synthesis can also be employed. For background on solid phase techniques, reference is made to Andreu, D., Merrifield, R. B., Steiner, H. and Boman, H. G., (1983) Proc. Natl. Acad. Sci USA 80, 6475–6479; Andreu, D., Merrifield, R. B., Steiner, H. and Boman, H. G., (1985) Biochemistry 24, 1683–1688; Fink, J., Boman, A., Boman, H. G., and Merrifield, R. B., (June 1989) Int. J. Peptide Protein Res. 33, 412–421; Fink, J., Merrifield, R. B., Boman, A. and Boman, H. G., (1989) J. Biol. Chem. 264, 6260–6267; each of which being hereby incorporated herein by reference.

The novel peptides of this invention are valuable antibacterial drugs for both Gram negative and Gram-positive organisms. They are especially valuable for treating infections caused by organisms that have developed resistance to commonly employed antibiotics. They are also active against malaria parasites, e.g. *Plasmodium falciparum*. Because of their great resistance to enzymatic degradation they can be administered orally as well as topically by intramuscular or intravenous injection.

Since the products of the invention are amphoteric they may be utilized as free bases, as acid addition salts or as metal salts. The salts must, of course, be pharmaceutically acceptable, and these will include metal salts particularly aklali and alkaline earth metal salts, suitably potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The activity of the products of the invention may be enhanced by coadministration with liposomes.

A further aspect of the present invention provides pharmaceutical compositions which comprise one or more compounds of the invention and a pharmaceutically acceptable carrier. The compositions may be made up of any pharmaceutical form appropriate for the desired route of administration. Examples of such compositions include solid compositions for oral administration such as tablets, capsules, pills, powders and granules. Liquid compositions for oral administration such as solutions, suspensions, syrups or elixirs and preparations for parenteral administration such as sterile solutions, suspensions or emulsions. The compositions may also be manufactured in the form of sterile solid compositions which can be dissolved in sterile water, physiological saline or some other sterile injectable medium immediately before use. Topical compositions, typically in the form of emulsions, suspensions, creams, lotions or foams which may contain emollients, suspending agents, chelating agents, stiffening agents, buffering agents, and other components conventionally used with topical compositions containing antibiotics may also be provided.

In all such compositions the antibiotic and/or antimalarial will normally be the principal physiologically active ingredient.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following non-limiting examples are given by way of illustration only and are not to be considered limitations of this invention, many apparent variations of which are possible without departing from the spirit or scope thereof.

EXAMPLES 1

Preparation of Peptides

Novel peptides of this invention are synthesized by a combination of automated (Applied Biosystem 430A) solid phase techniques (see articles regarding synthesis, cited supra). In particular, the novel peptides D-[CA(25–37)CA(1–13)], D-[M(1–13)CA(1–13)], D-[CA(1–11)CD(12–37)], D-[CA(1–24)M(1–13)], D-[CA(1–13)M(1–13)], and D-[M(16–26)M(1–13)] were prepared by the following standard double coupling protocol, based on 2.5 g of starting resin (0.21 mmol/g): (1) $CH_2Cl_2$, 50 mL, 4×1 min; (2) 50% TFA/$CH_2Cl_2$, 50 mL, 2×1 min; (3) 50% TFA/$CH_2Cl_2$, 50 mL, 1×20 min; (4) $CH_2Cl_2$, 50 mL, 6×1 min; (5) 5% DIEA/$CH_2Cl_2$, 50 mL, 2×2 min; (6) $CH_2Cl_2$, 50 mL, 6×1 min; (7) protected amino acid, 4 eq in 20 mL of $CH_2Cl_2$, add to reaction vessel, rinse with 4 mL of $CH_2Cl_2$, and shake at room temperature for 5 min; 4 eq of DCC in 3 mL of $CH_2Cl_2$, add to reaction vessel, rinse with 2 mL of $CH_2Cl_2$, and shake for 100 min at room temperature; (8) $CH_2Cl_2$, 50 mL, 4×1 min; (9) 5% DIEA/$CH_2Cl_2$. 50 mL, 1×2 min; (10) $CH_2Cl_2$, 50 mL, 4×1 min; (11) DMF, 50 mL, 2×2 min; (12) protected amino acid, 8 eq in 3 mL of $CH_2Cl_2$, 0° C. add DCC, 4 eq in 1 mL of $CH_2Cl_2$, 0° C., rinse with 1 mL of $CH_2I_2$, 0° C., after 10 min. at 0° C., filter, add 25 of DMF, 0° C., add to reaction vessel, rinse with 5 mL of DMF, 0° C., shake for 1 h at room temperature; (13) DMF, 50 mL, 2×2 min; (14) $CH_2Cl_2$, 50 mL, 4×1 min; (15) 5% DIEA/$CH_2Cl_2$, 50 mL, 1×2 min; (16) $CH_2Cl_2$, 50 mL, 4×1 min; (17) 3- to 5-mg sample for ninhydrin analysis. This protocol is repeated for subsequent amino acids to complete the assembly of the desired peptide.

The fully protected peptide on the resin is then treated with TFA to remove the $N^\alpha$ Boc group and dried. Cleavage of the peptide from the resin supports is accomplished by the low/high HF method, Tam et al (1983) *J. Am. Chem. Soc.* 105 6442–6455. Low HF is accomplished with 5 mL of HF/dimethyl sulfide/p-cresol/p-thiocresol (25:65:7.5:2.5), at 0° C. for 2 hr. High HF is accomplished with 10 mL of HF/p-cresol/p-thiocresol (95:3.75:1.25), at 0° C. for 1 hr. After evaporation of HF, the product is first washed with anhydrous ether to remove the scavengers, and then dissolved in 10% HOAc in water. The crude material is obtained by lyophilization.

As shown in Table 2, a number of compounds of the inventions were prepared and tested for activity against a variety of test organisms selected to represent a number of different types of pathogens some of them known to be particularly virulent by the inhibition zone assay of Hoffmann et al (1981) *Insect Biochem.* 11 537–548 which is incorporated herein by reference. Thin agar or agarose plates (8.5 cm diameter) were prepared with 6 ml of rich medium containing 100 ug/ml of streptomycin and $2 \times 10^5$ viable cells of a test organism resistant to streptomycin. Wells of 3.5 mm diameter were punched in the plates and 3 ul of serially diluted samples were placed in the wells. The diameters of the zones of inhibition around the wells were measured after overnight incubation at 30° or 37° C. For each peptide the squares of the zone diameters were plotted against the logarithm of the concentration, and from the slopes and intercepts the lethal concentrations were calculated as described by Hultmark (1983) *EMBO J.* 2, 571–76 or Hultmark et al (1982) *Eur. J. Biochem.* 127 207–217 each of which being incorporated herein by reference.

TABLE 2

| | | Lethal Concentrations (uM) for Peptides with L- or D-amino acids | | | | | | |
|---|---|---|---|---|---|---|---|---|
| # | Compound | D or L (aa) | D21 | OT97 | Bs11 | Bs11 +ME | Staph | Strep | SRC |
| 1 | CA(1–37) | L | 0.2 | 1 | 3 | 60 | >300 | 5 | >200 |
| 2 | CA(1–37) | D | 0.3 | 0.8 | 3 | 30 | >300 | 2 | >300 |
| 3 | CA(1–13)M(1–13) | L | 0.5 | 1 | 0.7 | 0.9 | 2 | 1 | >200 |
| 4 | CA(1–13)M(1–13) | D | 0.8 | 2 | 1 | 1 | 8 | 0.8 | 500 |
| 5 | CA(1–13)M(1–13) | D* | 0.9 | 7 | 2 | 30 | >400 | 4 | >400 |
| 6 | CA(1–8)M(1–18) | L | 0.3 | 0.7 | 0.4 | 0.5 | 1 | 2 | >600 |
| 7 | CA(1–8)M(1–18) | D | 0.3 | 0.6 | 0.2 | 0.2 | 0.3 | 0.8 | >400 |
| 8 | Mag2(1–23)–$NH_2$ | L | 4 | 30 | 3 | 8 | 300 | 4 | 300 |
| 9 | Mag2(1–23)–$NH_2$ | D | 1 | 30 | 3 | 4 | 100 | 3 | >400 |
| 10 | M(1–26) | L | 0.8 | 3 | 0.2 | 0.3 | 0.2 | 0.5 | 4–8 |
| 11 | M(1–26) | D | 1 | 2 | 0.4 | 0.3 | 0.1 | 0.9 | 2–3 |

Lethal Concentrations calculated from inhibition zones on thin agarose plates seeded with the respective organisms. D21: *E. coli*; OT97: *P. aeruginosa*; Bs11: *B. subtilis*; +ME: plates prepared with medium E; Staph: *S. aureus* Cowan 1; Strep: *S. pyogenes*; SRC: Sheep red cells.; *all amino acids are of the D configuration except Ile.

EXAMPLE 3

Figure 2:
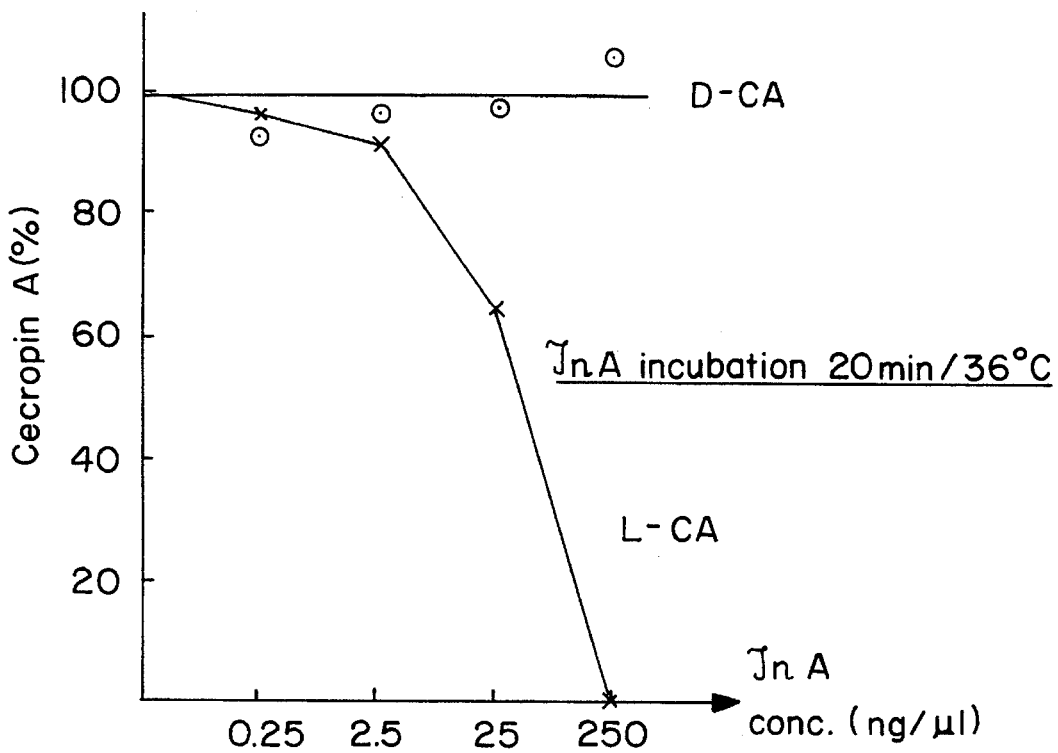
FIG. 2 is similar to FIG. 1 except that the proteolytic enzyme employed was immune inhibitor A (In A).

FIGS. 1 and 2 graphically illustrate the resistance of the compounds of this invention to enzymatic hydrolysis by trypsin or immune inhibitor A (In A). Table 3 lists the relevant data from which the graphs were prepared. The experiments were conducted as follows:

The original solutions of the enzymes contained 5 mg/ml in the case of trypsin and 0.1 mg/ml in the case of InA. These two samples were diluted as follows: A $10^{-1}$, B $10^{-2}$, C $10^{-3}$ and D $10^{-4}$. From each dilution, 2 ul were mixed with 2 ul of two peptides (D-CA and L-CA, both containing 1.3 ug/ul=162 pmol/ul). Control mixtures were made with 2 ul water and 2 ul peptide. All samples were incubated for 20 min at 36° C. Before and after the incubation, all samples were kept on ice. After the incubation 3 ul were placed in wells on plates seeded with *E. coli* D21 in order the determine the amount of antibiotic that was left. The diameter of the inhibition zone was recorded and compared with a previously prepared a standard curve. Results are as given in the table and illustrated in the figures.

TABLE 3

Comparison of the D- and L-forms of cecropin A for proteolytic resistance

| Substrate | | InA dilution | | | | Control (no Enzyme) | Standard Error |
|---|---|---|---|---|---|---|---|
| | | A | B | C | D | | |
| L-CA | Zone of inhibition (cm) | None | 1.42 | 1.48 | 1.49 | 1.49 | |
| | Amount of peptide left (pmol) | 0 | 316 | 442 | 469 | 469 | — |
| | Conc. (pmol/ul) | 0 | 105 | 147 | 156 | 156 | |
| | Percent remaining | 0 | 65 | 91 | 96 | 96 | |
| D-CA | Zone of inhibition (cm) | 1.54 | 1.52 | 1.52 | 1.51 | 1.55 | |
| | Amount of peptide left (pmol) | 512 | 468 | 468 | 448 | 535 | 10% |
| | Conc. (pmol/ul) | 171 | 156 | 156 | 149 | 178 | |
| | Percent remaining | 106 | 96 | 96 | 92 | 110 | |

| Substrate | | Trypsin Dilution | | | | Control | Standard Error |
|---|---|---|---|---|---|---|---|
| | | A | B | C | D | | |
| L-CA | Zone of inhibition (cm) | None | None | 0.93 | 1.25 | 1.45 | |
| | Amount of peptide left (pmol) | 0 | 0 | 34 | 131 | 373 | 27% |
| | Conc. (pmol/ul) | 0 | 0 | 11 | 44 | 124 | |
| | Percent remaining | 0 | 0 | 6.8 | 27 | 77 | |
| D-CA | Zone of inhibition (cm) | 1.55 | 1.53 | 1.54 | 1.53 | 1.54 | |
| | Amount of peptide left (pmol) | 535 | 489 | 512 | 489 | 512 | |
| | Conc. (pmol/ul) | 178 | 163 | 171 | 163 | 171 | 10% |
| | Percent remaining | 110 | 101 | 106 | 101 | 106 | |

What is claimed is:

1. A peptide comprising a hydrophilic or basic region and a hydrophobic region of an antibacterial and/or antimalarial peptide which is cecropin A, cecropin B, cecropin D, magainin or melittin, wherein the hydrophobic and hydrophilic regions comprise substantially all D-amino acids, but which may include up to 8 L amino acids, and wherein the peptide has the following properties:

a) antibiotic and/or antimalarial activity; and b) increased resistance to enzymatic hydrolysis compared to corresponding peptides containing only L-amino acids.

2. The peptide of claim 1, wherein the hydrophilic or basic region and the hydrophobic region are from the same antibacterial and/or antimalarial peptide.

3. The peptide of claim 1, wherein the hydrophilic or basic region and the hydrophobic region are from different antibacterial and/or antimalarial peptides.

4. The peptide of claim 1 consisting of about 20 to about 40 amino acid residues.

5. An antibacterial and/or antimalarial peptide comprising a hydrophilic or basic region and a hydrophobic region of an antibacterial and/or antimalarial peptide, wherein the hydrophobic and hydrophilic regions comprise substantially all D-amino acids but which may include up to 8 L amino acids, and wherein the peptide is cecropin A, cecropin B, cecropin D, melittin, magainin, D-[CA(1–13)Mag(13–23)], D-[Mag$_2$(13–23)CA(1–13)], D-[Mag$_2$(13–23)M(15–26), D-[M(1–13)CB(1–13], D-[M(1–15)C(1–11)], D-[CA(25–36)ProCA(1–13)], D-[CA(1–24)M(1–13)], D-[M(16–26)M(1–13)], D-[CA(1–24)M(16–26)], D-[CA(1–11)CD(12–37)], D-[CA(1–9)M(1–17)], D-[CA(1–17)M(1–9)], D-[M(1–13)CA(1–22)], D-[CA(1–13)M(1–13)], D-[Phe$^2$]CA, D-[Pro$^8$]CA, D-[M(15–26)Mag$_2$(13–23)], D-[Mag$_2$(13–23)Mag$_2$(1 . 12)], D-[Glu$^7$]M, D-M(1–12)ProCA(1–13)], D-[M(16–26)CA(14–37)], D-[CA(25–37)CA(1–13)l, D-[CA((1–13)M(1–13)], D-[M(16–26)CA(23–37)], D-[CB(25–35)M(14–26)], D-[CA(1–8)M(1–18)], D-CB(1–13)M(1–13)], D-[CA(1–18)M(1–8)], D-[M(1–13)CA(1–13)], D-[CA(1–13)Mag$_2$(13–23)], D-CA-OH, D-[M(16–26)M(1–13)], or D-[des Glu$^{19}$]Mag$_2$, and has the properties of:

a) antibiotic and/or antimalarial activity; and b) increased resistance to enzymatic hydrolysis compared to corresponding peptides containing only L-amino acids.

6. A pharmaceutical composition comprising the peptide of claim 1 and a suitable pharmaceutically acceptable carrier.

7. A pharmaceutical composition comprising the peptide of claim 5 and a suitable pharmaceutically acceptable carrier.

* * * * *